US011883332B2

United States Patent
Huh

(10) Patent No.: US 11,883,332 B2
(45) Date of Patent: Jan. 30, 2024

(54) EYE PROTECTION STRUCTURE

(71) Applicant: OTOS WING CO., LTD., Seoul (KR)

(72) Inventor: Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 327 days.

(21) Appl. No.: 17/413,745

(22) PCT Filed: Mar. 6, 2020

(86) PCT No.: PCT/KR2020/003186
§ 371 (c)(1),
(2) Date: Jun. 14, 2021

(87) PCT Pub. No.: WO2020/180154
PCT Pub. Date: Sep. 10, 2020

(65) Prior Publication Data
US 2022/0062052 A1 Mar. 3, 2022

(30) Foreign Application Priority Data
Mar. 6, 2019 (KR) .................. 10-2019-0025861

(51) Int. Cl.
*A61F 9/06* (2006.01)
*B23K 9/32* (2006.01)
*G02F 1/13* (2006.01)

(52) U.S. Cl.
CPC .............. *A61F 9/067* (2013.01); *B23K 9/322* (2013.01); *G02F 1/1313* (2013.01)

(58) Field of Classification Search
CPC ........................................................ A61F 9/06
See application file for complete search history.

(56) References Cited

U.S. PATENT DOCUMENTS

| 4,271,538 A | 6/1981 | Montesi et al. |
| 5,432,568 A | 7/1995 | Betz et al. |
(Continued)

FOREIGN PATENT DOCUMENTS

| CN | 101415467 A | 4/2009 |
| CN | 109069296 A | 12/2018 |
(Continued)

OTHER PUBLICATIONS

International Search Report and Written Opinion for PCT/KR2020/003186 dated Jun. 16, 2020, all pages.

(Continued)

*Primary Examiner* — Edmond C Lau
(74) *Attorney, Agent, or Firm* — Kilpatrick Townsend & Stockton LLP

(57) ABSTRACT

An embodiment of the present disclosure discloses an eye protection structure for protecting a worker, the eye protection structure including a window convex outward to cover both eyes of the worker, wherein the window includes a transmissive portion, the transmissive portion includes an inner surface facing the worker's face and an outer surface opposite to the inner surface, a first radius of curvature of the outer surface of the transmissive portion and a second radius of curvature of the inner surface of the transmissive portion are different from each other, and a thickness of a central portion of the transmissive portion is greater than a thickness of an edge portion of the transmissive portion.

11 Claims, 19 Drawing Sheets

(56) References Cited

U.S. PATENT DOCUMENTS

| | | | |
|---|---|---|---|
| 6,038,705 A | 3/2000 | Jarvis | |
| 2006/0000011 A1 | 1/2006 | Reichow et al. | |
| 2015/0272260 A1* | 10/2015 | Ryan | B32B 37/12 |
| | | | 156/60 |
| 2019/0125586 A1* | 5/2019 | Magnusson | G02F 1/133528 |
| 2019/0142640 A1* | 5/2019 | Magnusson | A61F 9/06 |
| | | | 2/421 |

FOREIGN PATENT DOCUMENTS

| | | |
|---|---|---|
| EP | 2 387 898 A1 | 11/2011 |
| EP | 3241533 A1 | 11/2017 |
| FR | 2688322 A1 | 12/1992 |
| JP | 5531043 B2 | 6/2014 |
| KR | 20-0383007 Y1 | 4/2005 |
| KR | 10-1288846 B1 | 7/2013 |
| KR | 0-1385831 B1 | 5/2014 |
| KR | 10-2019-0005908 A | 1/2019 |

OTHER PUBLICATIONS

Supplementary European Search Report for 20767272 dated Apr. 11, 2022, 8 pages.
First Office Action dated Dec. 1, 2022 for CN 202080006886.4, 8 pages.
Second Office Action dated Jun. 16, 2023 for CN 202080006886.4, 7 pages.

\* cited by examiner

EYE PROTECTION STRUCTURE

TECHNICAL FIELD

Embodiments of the present disclosure relate to an eye protection structure, and more specifically, to an eye protection structure including a window that transmits light.

BACKGROUND ART

A eye protection structure is worn to protect workers from light or high heat generated during welding processes such as arc welding. The eye protection structure has various shapes and structures, such as a shape covering the worker's eyes and the periphery of the eyes, and a shape covering a user's head.

DESCRIPTION OF EMBODIMENTS

Technical Problem

Workers may perform work such as welding by wearing a eye protection structure having a specific shape among various types of eye protection structures in consideration of the work purpose and environment. There is an inconvenience that the worker has to change the eye protection structure and wear it according to the work contents such as the welding part and the intensity of the spark used during welding.

The present disclosure is to solve various problems including the above problem, and embodiments of the present disclosure provide a welding protection system capable of easily changing its shape according to the work content and capable of protecting the worker's body in various ways. However, these problems are exemplary, and the scope of the present disclosure is not limited thereto.

Solution To Problem

An embodiment of the present disclosure discloses an eye protection structure for protecting a worker including a window convex outward to cover both eyes of the worker, wherein the window includes a transmissive portion, the transmissive portion includes an inner surface facing the worker's face and an outer surface opposite to the inner surface, a first radius of curvature of the outer surface of the transmissive portion and a second radius of curvature of the inner surface of the transmissive portion are different from each other, and a thickness of a central portion of the transmissive portion is greater than a thickness of an edge portion of the transmissive portion.

The second radius of curvature may be smaller than the first radius of curvature.

The second radius of curvature may depend on at least one of the first radius of curvature, the thickness of the central portion, and a refractive index of the transmissive portion.

The transmissive portion may satisfy the following conditions:

$$(R1-t1+t1/n)-1<R2<R1$$

wherein R1 represents the first radius of curvature, t1 represents the thickness of the central portion of the transmissive portion, n represents the refractive index of the transmissive portion, and R2 represents the second radius of curvature.

The window may include a resin material.

A center of the first radius of curvature and a center of the second radius of curvature may be apart from each other.

The window further may include a rib disposed inside the transmissive portion.

The rib may extend along a direction crossing the inner surface of the transmissive portion.

The window may further include an opaque portion having a smaller transmittance than the transmissive portion.

The opaque portion may entirely surround the transmissive portion.

Aspects, features, and advantages other than those described above will become apparent from the following drawings, claims, and detailed description of the disclosure.

Advantageous Effects of Disclosure

The eye protection structure according to the embodiments of the present disclosure may protect the user's eyes even when used for a long time, and prevent the user's eyesight deterioration and fatigue accumulation. The above-described effects are exemplary, and detailed effects according to embodiments will be described later.

MODE OF DISCLOSURE

Figure 1:
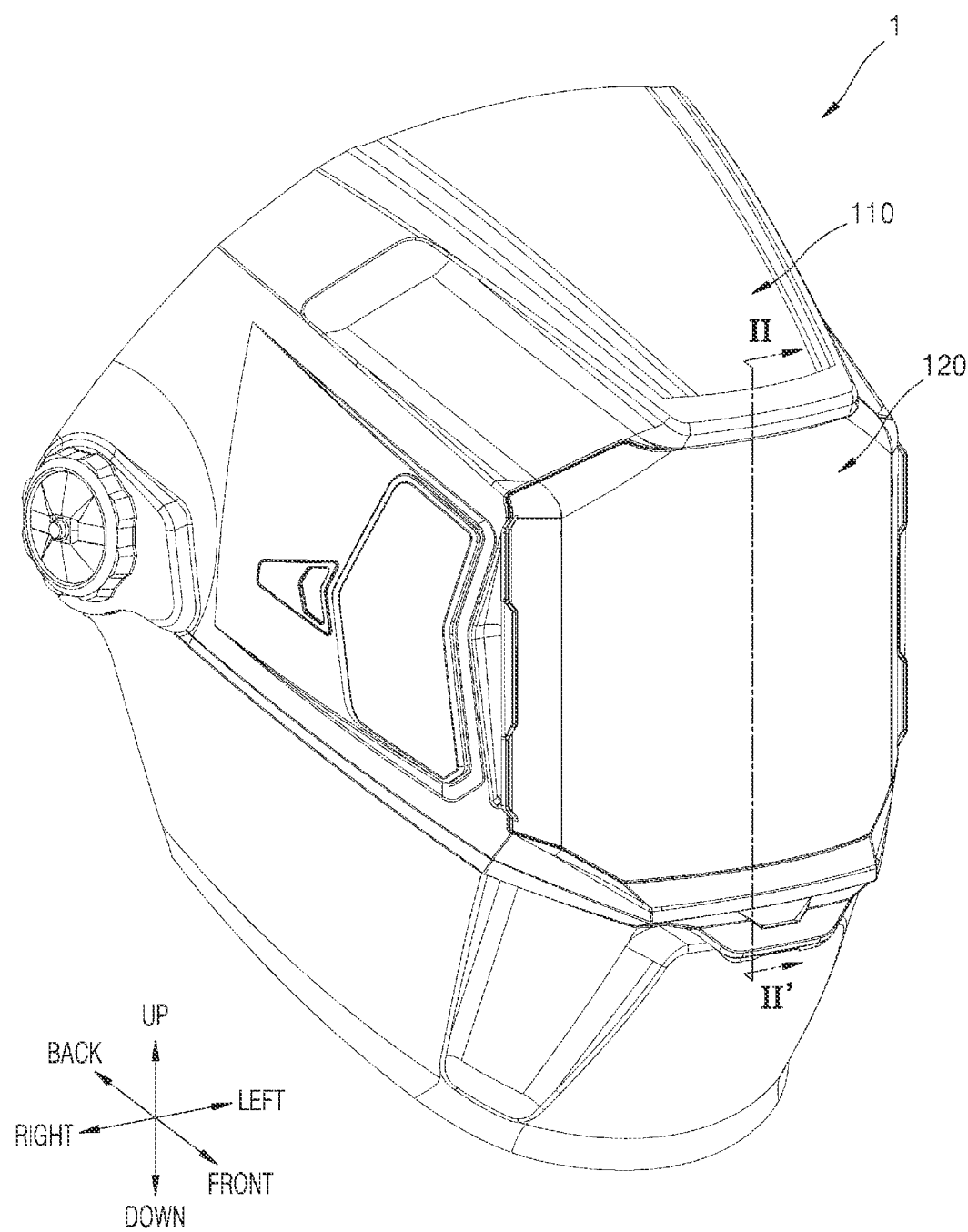
FIG. 1 is a perspective view schematically illustrating an eye protection structure according to an embodiment of the present disclosure.

In the present disclosure, since various transformations can be applied and various embodiments may be provided, specific embodiments are illustrated in the drawings and will be described in detail in the detailed description. Effects and features of the present disclosure, and a method of achieving them will be apparent with reference to embodiments described later in detail together with the drawings. However, the present disclosure is not limited to the embodiments disclosed below and may be implemented in various forms.

Hereinafter, embodiments of the present invention will be described in detail with reference to the accompanying drawings, and when describing with reference to the drawings, the same or corresponding constituent elements are assigned the same reference numerals, and redundant descriptions thereof will be omitted.

In the following embodiments, terms such as first and second are not used in a limiting meaning, but are used for the purpose of distinguishing one component from another component.

In the following examples, expressions in the singular include plural expressions unless the context clearly indicates otherwise.

In the following embodiments, terms such as include or have means that the features or elements described in the specification are present, and do not preclude the possibility that one or more other features or components may be added.

In the following embodiments, when a part such as a region or a component is on or above another part, it includes not only the case where the part is directly above the other part, but also the case in which the other part is disposed on the part with a region, component, etc. therebetween.

In the drawings, for convenience of description, the size of the constituent elements may be exaggerated or reduced. For example, the size and thickness of each component shown in the drawings are arbitrarily shown for convenience of description, and thus the present disclosure is not necessarily limited to what is shown.

When a certain embodiment may be implemented differently, a specific process order may be performed differently from the described order. For example, two processes described in succession may be performed substantially simultaneously, or may be performed in an order opposite to the described order.

In the following embodiments, when a region, a component, etc. are connected, it includes not only the case where the region and the constituent elements are directly connected, but also the case where the other region and the constituent elements are interposed and indirectly connected between the region and the elements.

Figure 2:
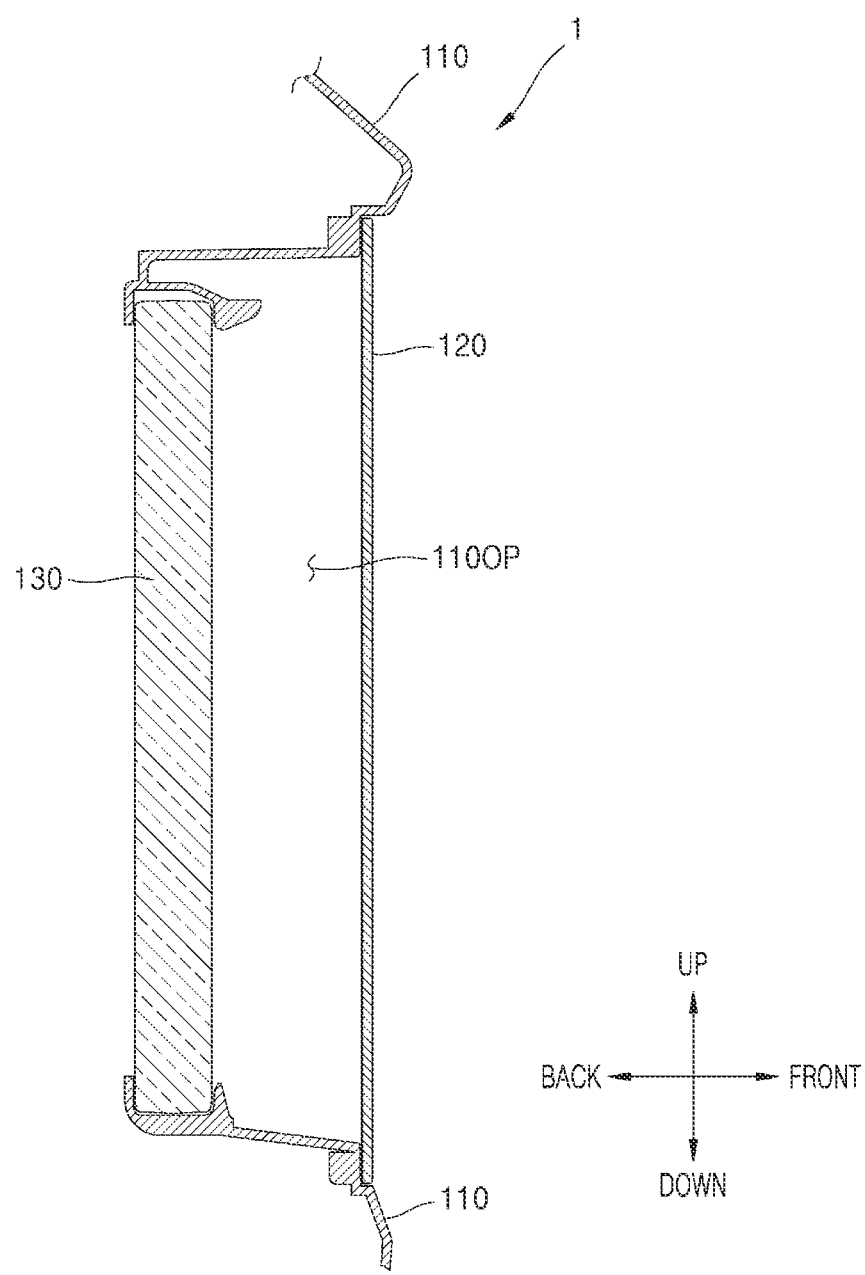
FIG. 2 is a cross-sectional view taken along line II-II of FIG. 1.
Figure 3:
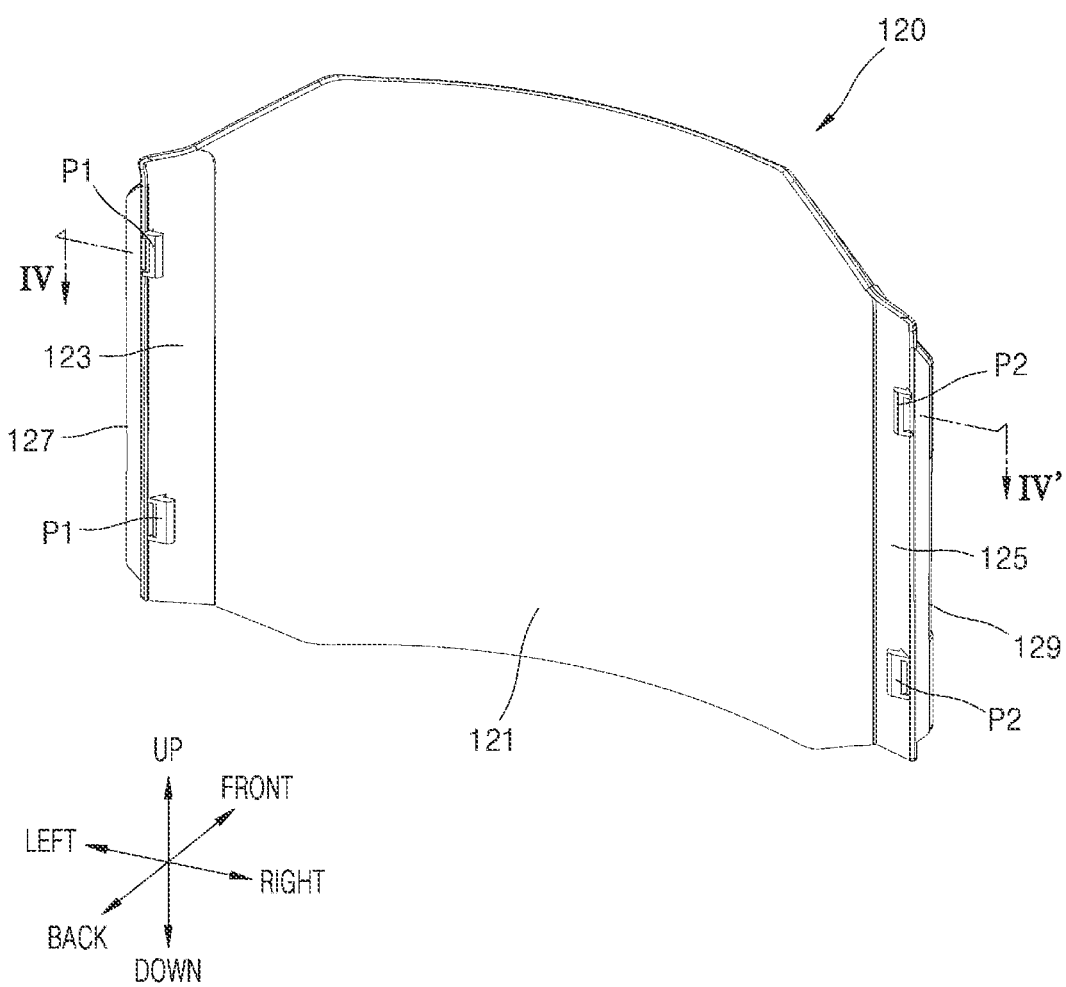
FIG. 3 is a rear perspective view illustrating a window according to an embodiment of the present disclosure.
Figure 4:
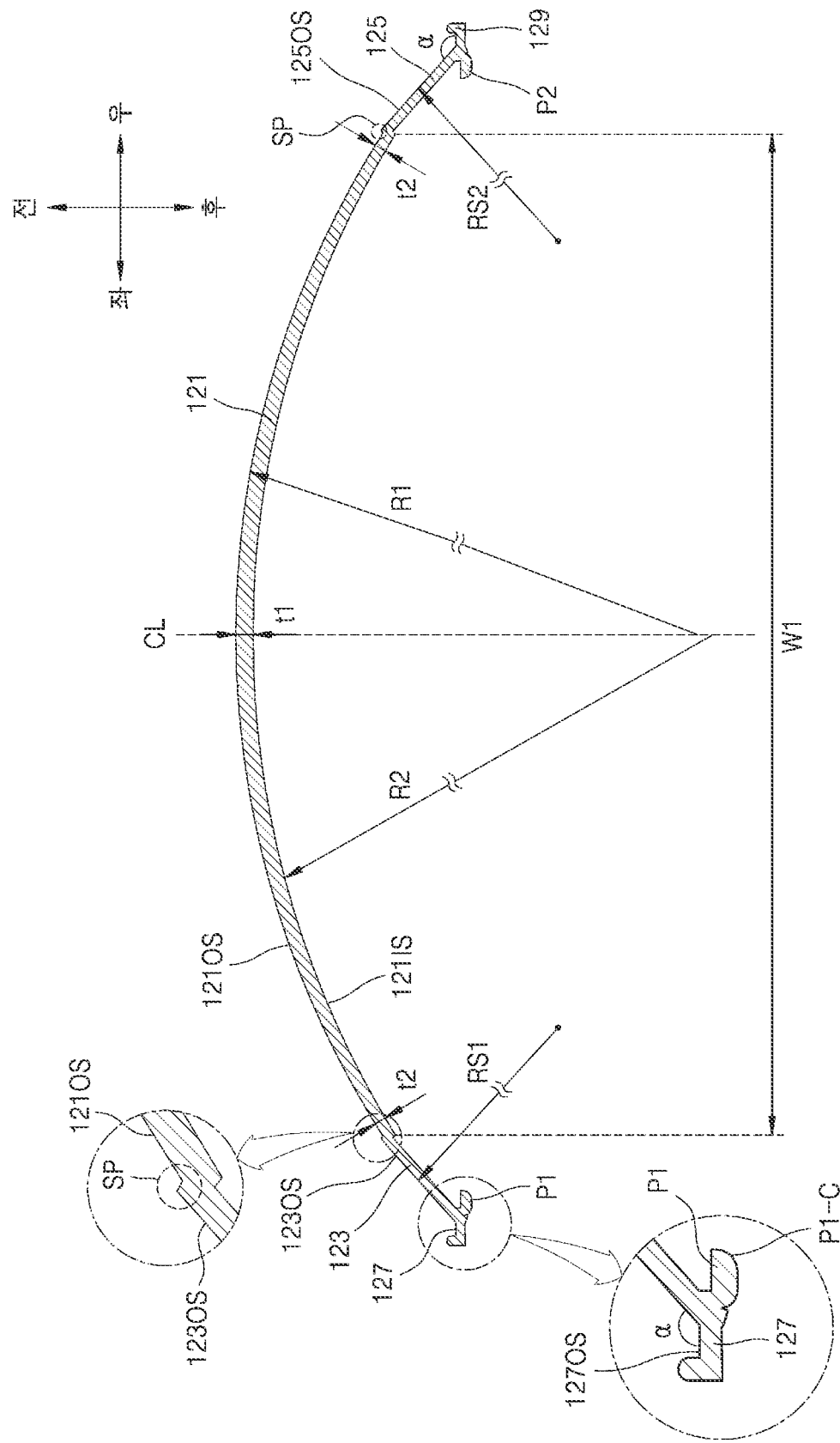
FIG. 4 is a cross-sectional view taken along line IV-IV' of FIG. 3.
Figure 5A:
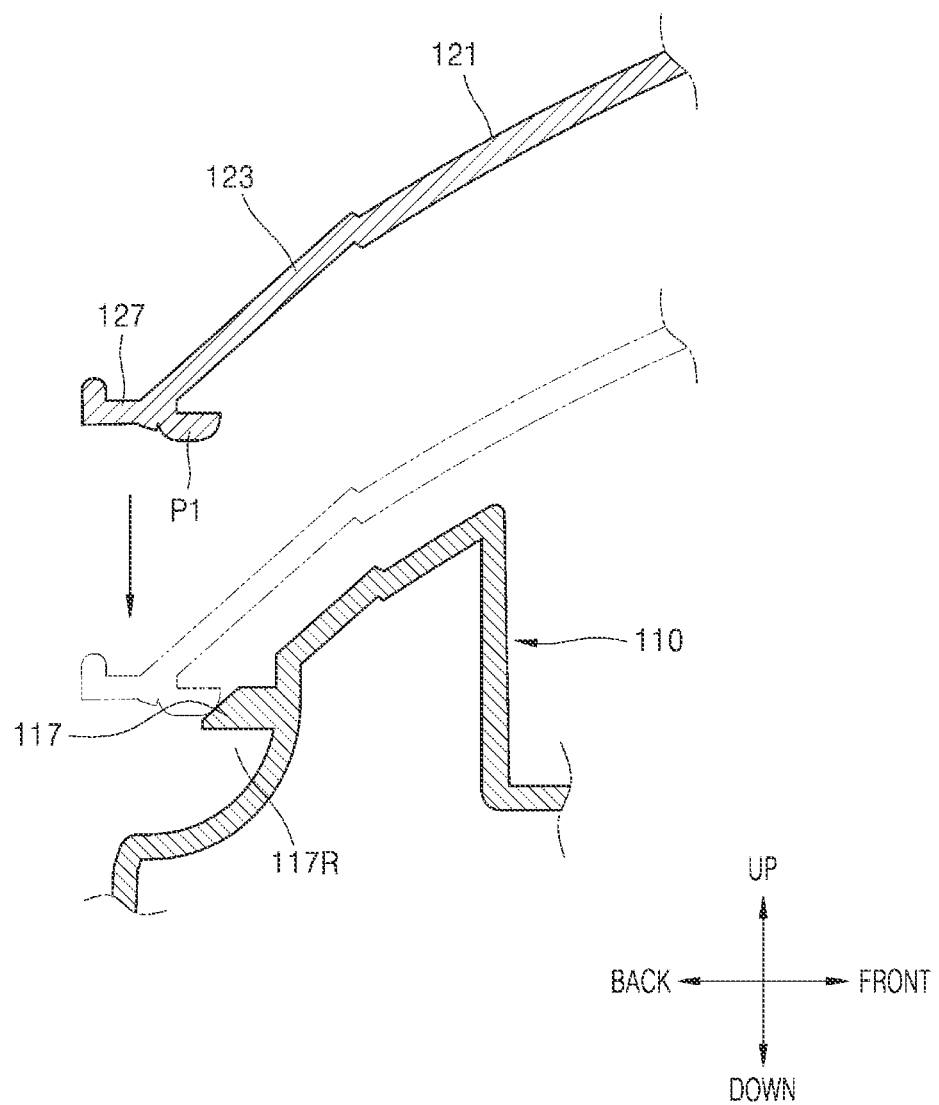
FIGS. 5A and 5B are cross-sectional views illustrating a coupling of the window and a main body in the eye protection structure according to an embodiment of the present disclosure.
Figure 5B:
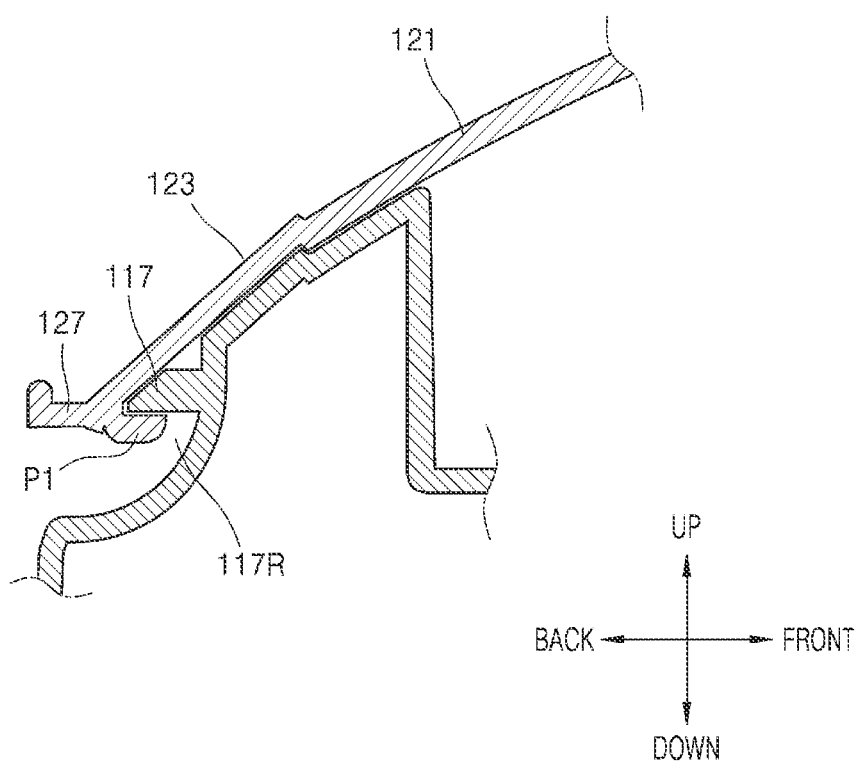

FIG. 1 is a perspective view schematically illustrating an eye protection structure according to an embodiment of the present disclosure, FIG. 2 is a cross-sectional view taken along line II-II of FIG. 1, FIG. 3 is a rear perspective view illustrating a window according to an embodiment of the present disclosure, FIG. 4 is a cross-sectional view taken along line IV-IV' of FIG. 3, and FIGS. 5A and 5B are cross-sectional views illustrating a coupling of the window and a main body in the eye protection structure according to an embodiment of the present disclosure.

Referring to FIG. 1, the eye protection structure 1 may protect a workers body, for example, the workers eyes or the worker's face from external foreign objects or light generated during work. The eye protection structure 1 may include a main body 110 and a transparent window 120 coupled to the main body 110.

The main body 110 may include a polymer resin having a predetermined rigidity. For example, the main body 110 may be formed of a material having a predetermined strength, such as plastic, but the present disclosure is not limited thereto, and any material that is resistant to elements such as sparks that may occur during welding may be used. The main body 110 may be fixed to the head of the worker through a fixing member (not illustrated) provided inside the main body 110, and the fixing member may have a structure including a plurality of ribs such as a head band, and an element including a soft material such as a fibrous material or a cushion material may be disposed on at least a portion of the inner surface that is in direct contact with the head of the worker.

Referring to FIGS. 1 and 2, an opening 1100P may be provided in a region of the main body 110 corresponding to the user's eyes, and the opening 1100P may be covered by the window 120. The window 120 has a structure attachable to and detachable from the main body 110, and one of the main body 110 and the window 120 may have a coupling protrusion, and the other may have a groove into which the coupling protrusion is inserted.

In order to check the working situation with the naked eye, the window 120 may include a material through which light may transmit, for example, a transparent material. For example, the window 120 may include a resin material such as polycarbonate or acrylic, and may be molded by injection molding.

When the worker performs a task in which very bright light is instantaneously generated, such as welding, the eye protection structure 1 may include a blackening filter unit 130 (FIG. 2). The blackening filter unit 130 is disposed inside the window 120 and may overlap the window 120. The blackening filter unit 130 may include, for example, a liquid crystal display panel (LCD panel) capable of adjusting a degree of blackening according to an alignment direction of liquid crystals. In one embodiment, the degree of blackening of the blackening filter unit 130 may be manually adjusted according to the selection or request of the worker. Alternatively, the degree of blackening of the blackening filter unit 130 may be automatically adjusted according to the brightness of the welding light. When the degree of blackening is automatically adjusted according to the brightness of the welding light, optical sensors may be disposed on the outer surface of the eye protection structure 1. The intensity of light detected by the optical sensor is transmitted to a controller, and the controller may control the degree of blackening of the blackening filter unit 130 based on a signal for the received intensity of light.

Referring to FIG. 3, the window 120 may include a transmissive portion 121 and a first wing portion 123 and a second wing portion 125 disposed on both sides of the transmissive portion 121, respectively. The area of the transmissive portion 121 may be about 70% or more, 75% or more, 80% or more, or 85% or more of the area of the window 120.

The first wing portion 123 and the second wing portion 125 may have curvatures that are different from that of the transmissive portion 121. As an embodiment, as illustrated in FIG. 4, a first radius of curvature R1 of an outer surface 121OS of the transmissive portion 121 may be greater than a radius of curvature RS1 of an outer surface 123OS of the first wing portion 123, and may be greater than a radius of curvature RS2 of an outer surface 125OS of the second wing portion 125. The radius of curvature RS1 of the outer surface 123OS of the first wing portion 123 and the radius of curvature RS2 of the outer surface 125OS of the second wing portion 125 may be the same.

Curvatures of the outer surface 121OS of the transmissive portion 121 and an inner surface 121IS of the transmissive portion 121 may be different from each other. For example, the first radius of curvature R1 of the outer surface 121OS of the transmissive portion 121 may have a value greater than a second radius of curvature R2 of the inner surface 121IS of the transmissive portion 121. A first thickness t1 of a center portion of the transmissive portion 121 may be greater than a second thickness t2 of an edge portion of the transmissive portion 121. Here, the first thickness t1 of the center portion represents a thickness of a portion passing through a virtual center line CL illustrated in FIG. 4, and the virtual center line CL represents a virtual line extending along the left and right directions and passing through the center of the transmissive portion 121 as illustrated in FIG. 4.

The outer surface 123OS of the first wing portion 123 and the outer surface 125OS of the second wing portion 125 may form a step difference with respect to the outer surface 121OS of the transmissive portion 121, respectively. As illustrated in the enlarged view of FIG. 4, the outer surface 123OS of the first wing portion 123 may be positioned at a position protruding further toward the front than the outer surface 121OS of the transmissive portion 121. Accordingly, a step portion SP may be formed between the outer surface 123OS of the first wing portion 123 and the outer surface 121OS of the transmissive portion 121. Likewise, the outer surface 125OS of the second wing portion 125 may be positioned at a position protruding further forward the front than the outer surface 121OS of the transmissive portion 121. Accordingly, a step portion SP may be formed between the outer surface 125OS of the second wing portion 125 and the outer surface 121OS of the transmissive portion 121.

A width W1 of the transmissive portion 121 in the horizontal direction may be 100 mm to 200 mm, 120 mm to 180 mm, 130 mm to 180 mm, or 140 mm to 170 mm. The width W1 of the transmissive portion 121 in the horizontal direction may be a distance between the step portions SP disposed along the horizontal direction (or left and right direction).

A first side-end portion 127 may be positioned on one side of the first wing portion 123. The first side-end portion 127 is located on the opposite side of the transmissive portion 121 with respect to the first wing portion 123. The first side-end portion 127 is extended from the one side of the first wing portion 123, a first angle α between an outer surface 127OS of the first side-end portion 127 and the outer surface 123OS of the first wing portion 123 may be an obtuse angle.

Similarly, a second side-end portion 129 may be positioned on one side of the second wing portion 125. The second side-end portion 129 is located on the opposite side of the transmissive portion 121 with respect to the second wing portion 125. The second side-end portion 129 is extended from the one side of the second wing portion 125, a first angle α between the outer surface 129OS of the second side-end portion 129 and the outer surface 125OS of the second wing portion 125 may be an obtuse angle.

At least one first protrusion P1 extending toward the inside of the window 120 may be positioned around a coupling position between the first side-end portion 127 and the first wing portion 123. In an embodiment, when the number of first protrusions P1 is two or more, the first protrusions P1 may be apart from each other along a vertical direction (or up and down direction) as illustrated in FIG. 3.

Similarly, at least one second protrusion P2 extending toward the inside of the window 120 may be positioned around a coupling position between the second side-end portion 129 and the second wing portion 125. In an embodiment, when the number of second protrusions P2 is two or more, the second protrusions P2 may be apart from each other along a vertical direction (or up and down direction) as illustrated in FIG. 3.

As described above, the window 120 may be attachable to and detachable from the main body 110 (FIGS. 1 and 2), and the first protrusion P1 may have a curved surface P1-C as illustrated in the enlarged view of FIG. 4 so that the window 120 is easily coupled to the main body 110. Likewise, the second protrusion P2 may also include a curved surface.

As illustrated in FIG. 5A, the window 120 may be coupled with the main body 110 by a force pushing the window 120 while proceeding toward the main body 110. In this case, the first protrusion P1 may be accommodated in a recess 117R formed under a coupling piece 117 provided in the main body 110. The first protrusion P1 may be accommodated in the recess 117R while being moved while being in contact with one side of the coupling piece 117 as sliding along the curved surface P1-C.

Referring to FIG. 5B, when the window 120 is coupled to the main body 110, the coupling piece 117 may be positioned between the first protrusion P1 and the inner surface of the first wing portion 123. The structure that the first protrusion P1 is coupled to the main body 110 described with reference to FIGS. 5A and 5B may be equally applied to the second protrusion P2.

The user wearing the eye protection structure 1 may recognize an object or person disposed outside the window 120 through the window 120. As described above, the window 120 is formed of the resin material such as polycarbonate or acrylic, and since the window 120 including the above-described material has a refractive index different from that of air, the image that the user sees through the window 120 may be distorted, and the fatigue of the user's eyes may be increased. However, according to the exemplary embodiment of the present disclosure, the above-described problem may be solved by designing the transmissive portion 121 to have features to be described later.

Figure 6:
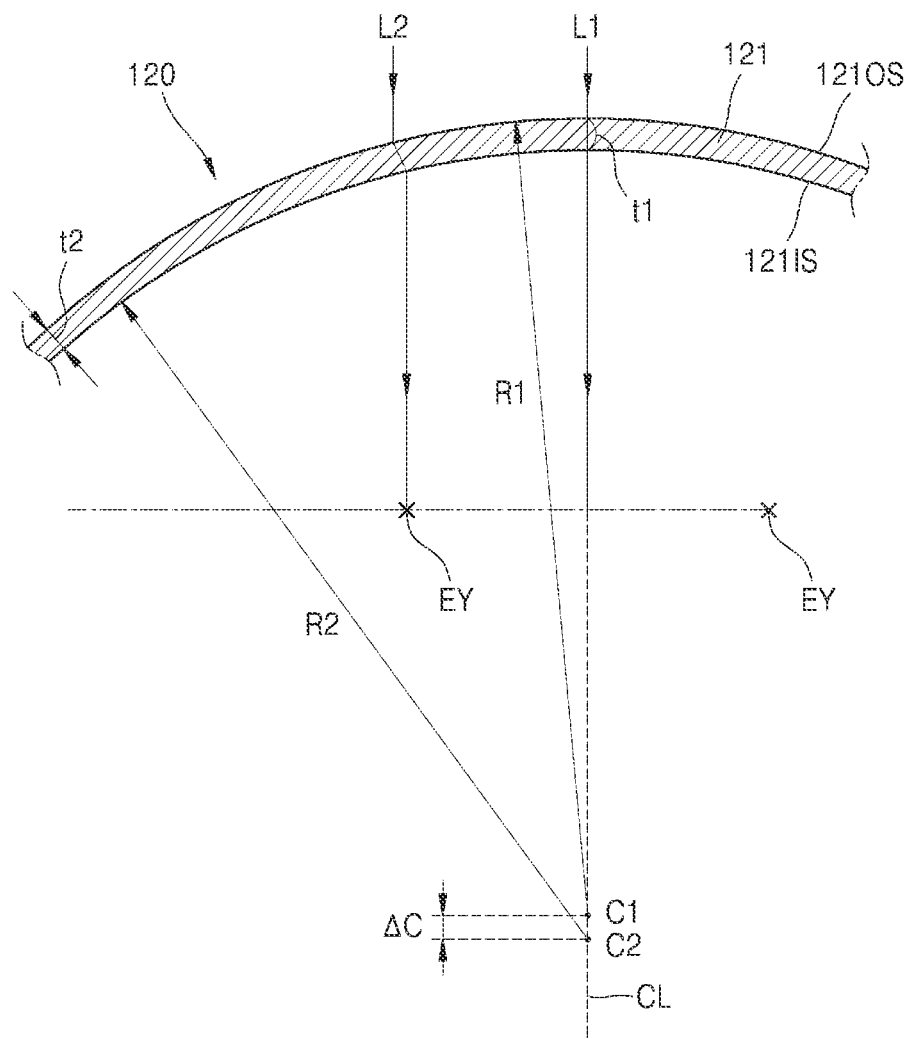
FIG. 6 is a cross-sectional view illustrating a portion of a transmissive portion according to an embodiment of the present disclosure.

FIG. 6 is a cross-sectional view illustrating a portion of a transmissive portion according to an embodiment of the present disclosure.

Referring to FIG. 6, the first radius of curvature R1 (unit: mm) of the outer surface 121OS of the transmissive portion 121 may be greater than the second radius of curvature R2 of the inner surface 121IS. For example, the first radius of curvature R1 may be selected in the range of 100 mm to 200 mm.

The first radius of curvature R1 (unit: mm), the second radius of curvature R2 (unit: mm) and the first thickness t1 (unit: mm) may satisfy Equation 1 below.

$$(R1-t1+t1/n)-1 < R2 < R1 \qquad \text{(Equation 1)}$$

Here, n represents a refractive index of the transmissive portion 121.

When the first radius of curvature R1 (unit: mm), the second radius of curvature R2 (unit: mm), and the first thickness t1 (unit: mm) satisfy the Equation 1, like a first light L1, since a second light L2 passing through a portion offset by a predetermined distance from the virtual center line CL passing through the center of the transmissive portion 121 also proceeds in parallel toward the user's eye EY, the user may experience a similar experience to perceive the outside with the naked eye, and eye fatigue may be reduced even when working for a long time.

As described above, the first thickness t1 of the center portion of the transmissive portion 121 is greater than the second thickness t2 of the edge portion of the transmissive portion 121. For example, the first thickness t1 may be formed to satisfy 1 mm<t1<2.6 mm, 1.5 mm<t1<2.6 mm, 2.0 mm<t1<2.6 mm, 2.1 mm≤t1≤2.5 mm, or 2.1 mm≤t1≤2.4 mm. The second thickness t2 may be at least 1.0 mm. For example, the second thickness t2 may be formed to satisfy 1.0 mm≤t2≤1.5 mm. When the first thickness t1 is smaller than the lowermost value, it is difficult to form the window 120 and a defective rate is increased, and when the first thickness t1 is greater than the uppermost value, the weight of the window 120 is increased and it may be difficult to implement the lightweight eye protection structure 1.

A center of the first radius of curvature R1 (hereinafter, referred to as a first center, C1) and a center of the second radius of curvature R2 (hereinafter, referred to as a second center, C2) are located on the same virtual line, for example, the virtual center line CL passing through the center of the transmissive portion 121, and may be apart from each other. A distance C between the first center C1 and the second center C2 may be smaller than the first thickness t1. When the distance C between the first center C1 and the second center C2 is equal to the first thickness t1 or greater than the first thickness t1, distortion of the image recognized by the user through the transmissive portion 121 may occur severely, thereby tiring the user's eyes.

A center of the first radius of curvature R1 (hereinafter, referred to as a first center, C1) and a center of the second radius of curvature R2 (hereinafter, referred to as a second center, C2) are located on the same virtual line, for example, the virtual center line CL passing through the center of the transmissive portion 121, and may be apart from each other. A distance C between the first center C1 and the second center C2 may be smaller than the first thickness t1. When the distance C between the first center C1 and the second center C2 is equal to the first thickness t1 or greater than the first thickness t1, distortion of the image recognized by the user through the transmissive portion 121 is severely generated, and it may tire the user's eyes.

Figure 7A:
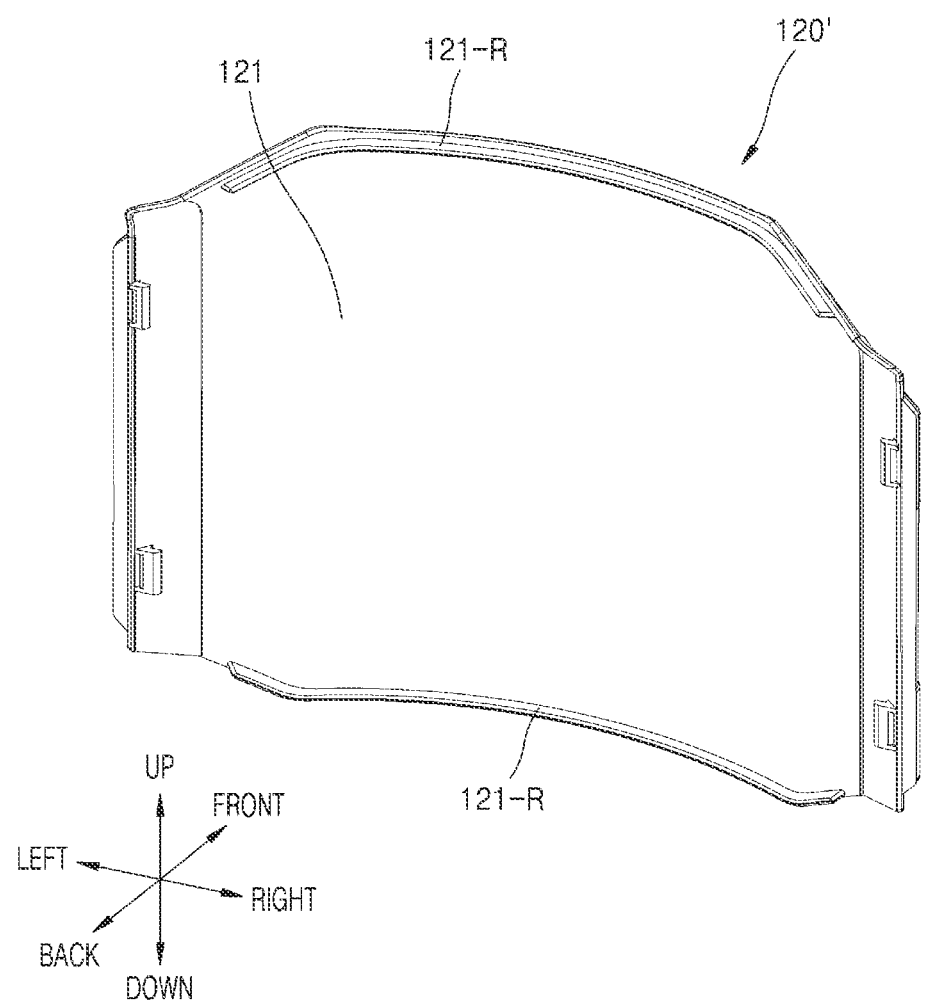
FIG. 7A is a schematic perspective view of a window according to another embodiment of the present disclosure.
Figure 7B:
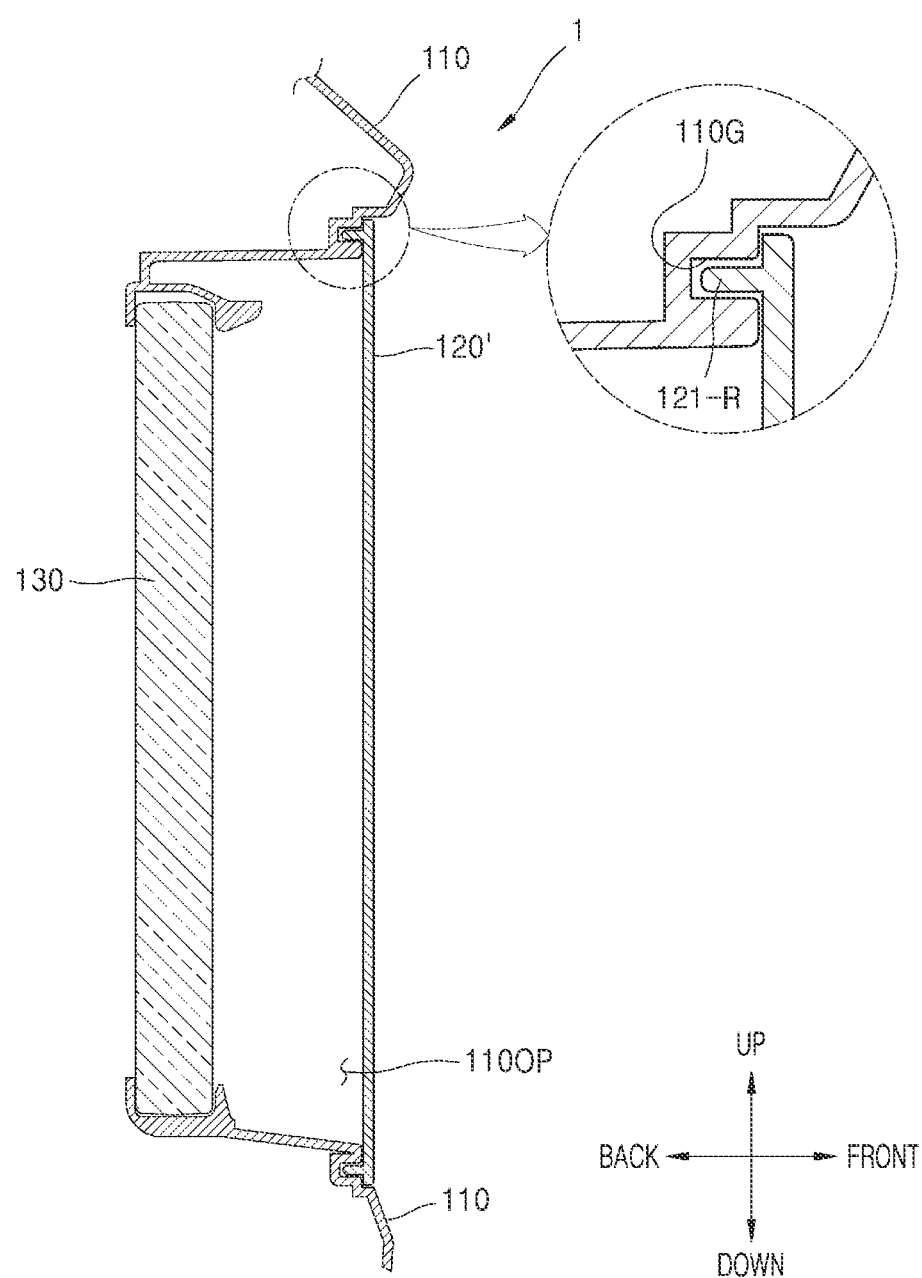
FIG. 7B is a cross-sectional view schematically illustrating a state in which the window is coupled to a main body according to another embodiment of the present disclosure.

FIG. 7A is a schematic perspective view of a window according to another embodiment of the present disclosure, and FIG. 7B is a cross-sectional view schematically illustrating a state in which the window is coupled to a main body according to another embodiment of the present disclosure.

Referring to FIG. 7A, a window 120' includes the same features as the window 120 described with reference to FIGS. 3 to 6, and may further include at least one rib 121-R positioned inside the transmissive portion 121.

The at least one rib 121-R may extend to have a predetermined width in a direction crossing the inner surface of the transmissive portion 121, for example, toward the inside of the transmissive portion 121. In one embodiment, FIG. 7A illustrates that the ribs 121-R are disposed above and below the transmissive portion 121, respectively. Each of the ribs 121-R may extend along an upper edge and a lower edge of the transmissive portion 121.

Each of the ribs 121-R may be injection molded integrally with the transmission portion 121. When the user wearing the eye protection structure 1 performs a work that generates high temperature heat such as welding, the rib 121-R prevents the window 120' from being deformed by radiant heat generated during work, and may applied a predetermined strength to the window 120'.

As described above with reference to FIGS. 1 and 2, the window 120' may be coupled to the main body 110. Referring to FIG. 7B, the ribs 121-R of the window 120' may be respectively accommodated in grooves 110G provided in the main body 110.

The features of rib 121-R described with reference to FIGS. 7A and 7B may also be applied to a window to be described later with reference to FIG. 8.

Figure 8:
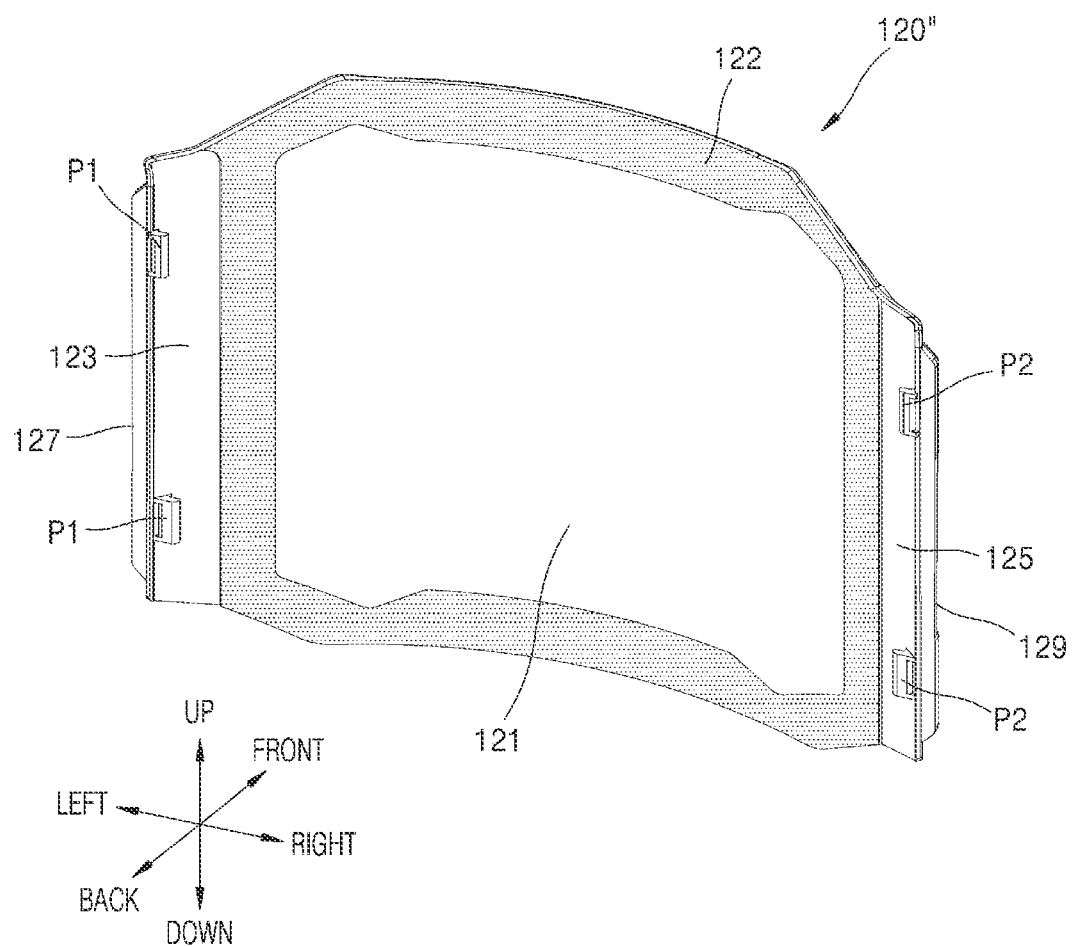
FIG. 8 is a schematic perspective view of a window according to another embodiment of the present disclosure.
Figure 9:
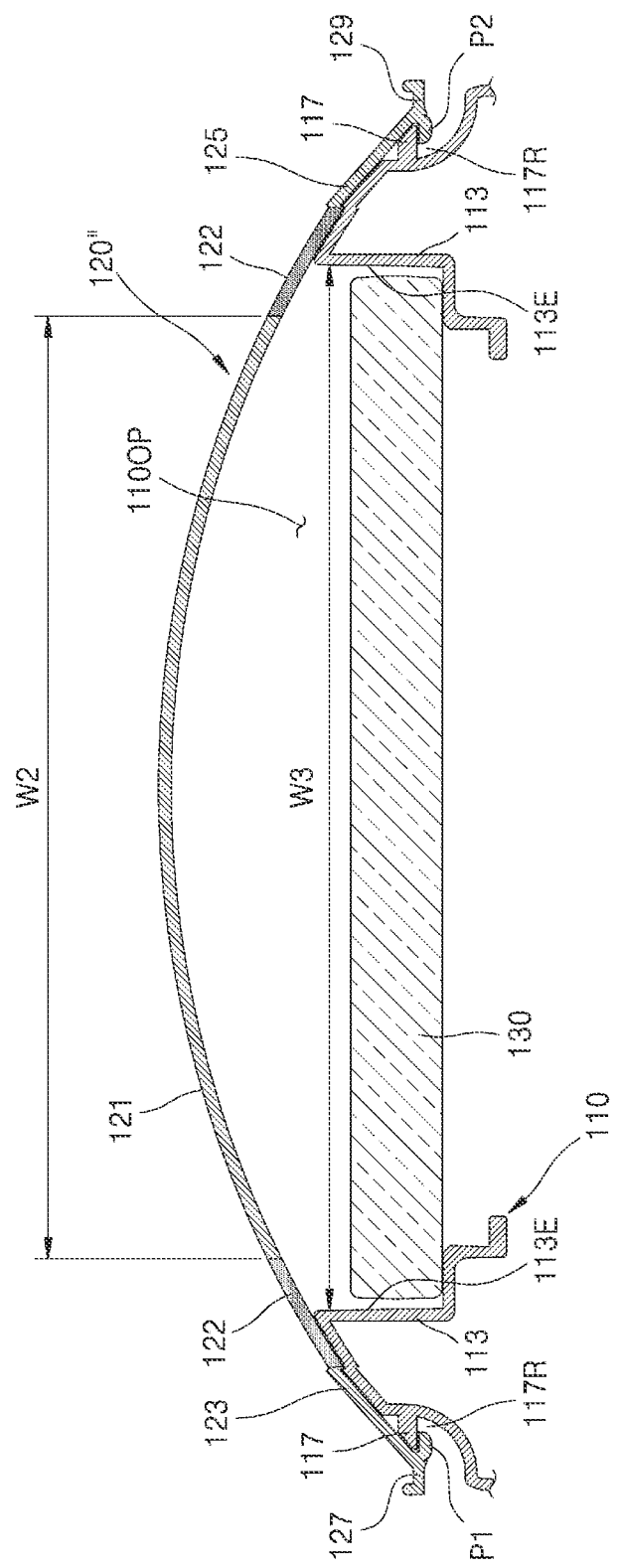
FIG. 9 is a cross-sectional view in a state in which the window is coupled to a main body according to another embodiment of the present disclosure.
Figure 10A:
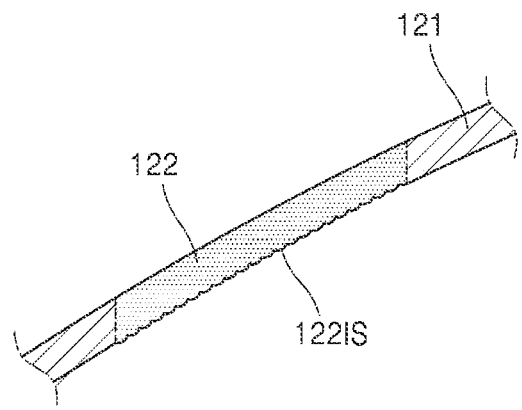
FIGS. 10A and 10B are cross-sectional views illustrating an enlarged opaque portion of a window according to an exemplary embodiment of the present disclosure.
Figure 10B:
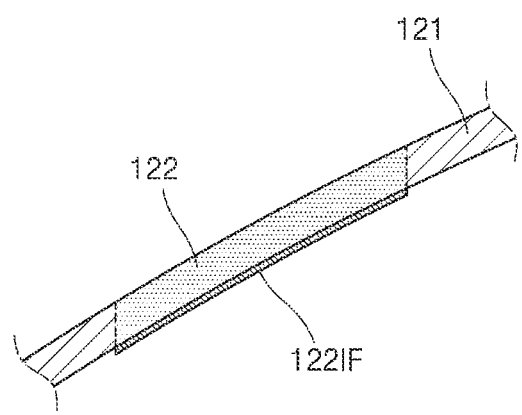

FIG. 8 is a schematic perspective view of a window according to another embodiment of the present disclosure, FIG. 9 is a cross-sectional view in a state in which the window is coupled to a main body according to another embodiment of the present disclosure, FIGS. 10A and 10B are cross-sectional views illustrating an enlarged opaque portion of a window according to an exemplary embodiment of the present disclosure.

A window 120" of FIG. 8 may include the same features as the window 120 described above with reference to FIGS. 3 to 6, and the differences will be described below. The window 120" may include an opaque portion 122 disposed adjacent to the transmissive portion 121. The opaque portion 122 may be positioned between the transmissive portion 121 and the first wing portion 123, and between the transmissive portion 121 and the second wing portion 125. The transmissive portion 121 may be entirely surrounded by the opaque portion 122.

Referring to FIG. 9, the window 120" may be coupled to the main body 110. For example, the window 120" may include the first protrusion P1 and the second protrusion P2 for coupling with the main body 110, and the coupling relationships thereof are as described above with reference to FIGS. 5A and 5B. For example, the main body 110 may include the at least one pair of coupling pieces 117, one coupling piece 117 may be positioned between the first protrusion P1 and the first wing portion 123, the other coupling piece 117 may be positioned between the second protrusion P2 and the second wing portion 125.

The window 120" may be arranged to cover the opening 110OP of the main body 110 as illustrated in FIG. 9, and the opening 110OP may be defined by a frame portion 113 of the main body 110. A width W3 of the opening 110OP may be greater than a width of the transmissive portion 121 (or a width between the opaque portions, W2). Accordingly, an inner wall 113E of the frame portion 113 defining the opening 110OP of the main body 110 may be covered by the opaque portion 122.

The blackening filter unit 130 may be accommodated in the frame portion 113, and, in this case, a fine gap may be formed between the inner wall 113E of the frame portion 113 and the blackening filter unit 130 due to an assembly tolerance. During work such as welding, heat or light may be transmitted to the user through the gap, but in the embodiment of the present disclosure, the opaque portion 122 is arranged to cover the fine gap formed between the inner wall 113E of the frame portion 113 and the blackening filter unit 130, so that the above-described problem may be avoided.

The opaque portion 122 may block or reflect light generated during welding, and may reflect radiant heat during welding. In one embodiment, the opaque portion 122 may include an uneven surface. For example, as illustrated in FIG. 10A, the uneven surface may be formed on an inner surface 122IS (or rear surface) of the opaque portion 122. Due to the above-described uneven structure, the transmittance of the opaque portion 122 may be smaller than the transmittance of the transmissive portion 121, and light generated during welding may be diffusely reflected. FIG. 10A discloses that an unevenness is formed on the inner surface 122IS of the opaque portion 122, but the present disclosure is not limited thereto. As another embodiment, a fine unevenness may be formed on an outer surface 122OS of the opaque portion 122.

In another embodiment, the opaque portion 122 may include a film 122IF, as illustrated in FIG. 10B. The film 122IF may be attached to an inner surface of the window 120" corresponding to the opaque portion 122 by an adhesive layer. FIG. 10B illustrates that the film 122IF is positioned on the inner surface of the opaque portion 122, but the present disclosure is not limited thereto. In another embodiment, the film 122IF may be positioned on the outer surface of the opaque portion 122.

The eye protection structure 1 described with reference to FIGS. 1 to 10B has been described as having an area covering the user's face in the remaining areas excluding the opening 110OP (FIG. 2, etc.) of the main body 110, but the present disclosure is not limited thereto.

Figure 11:
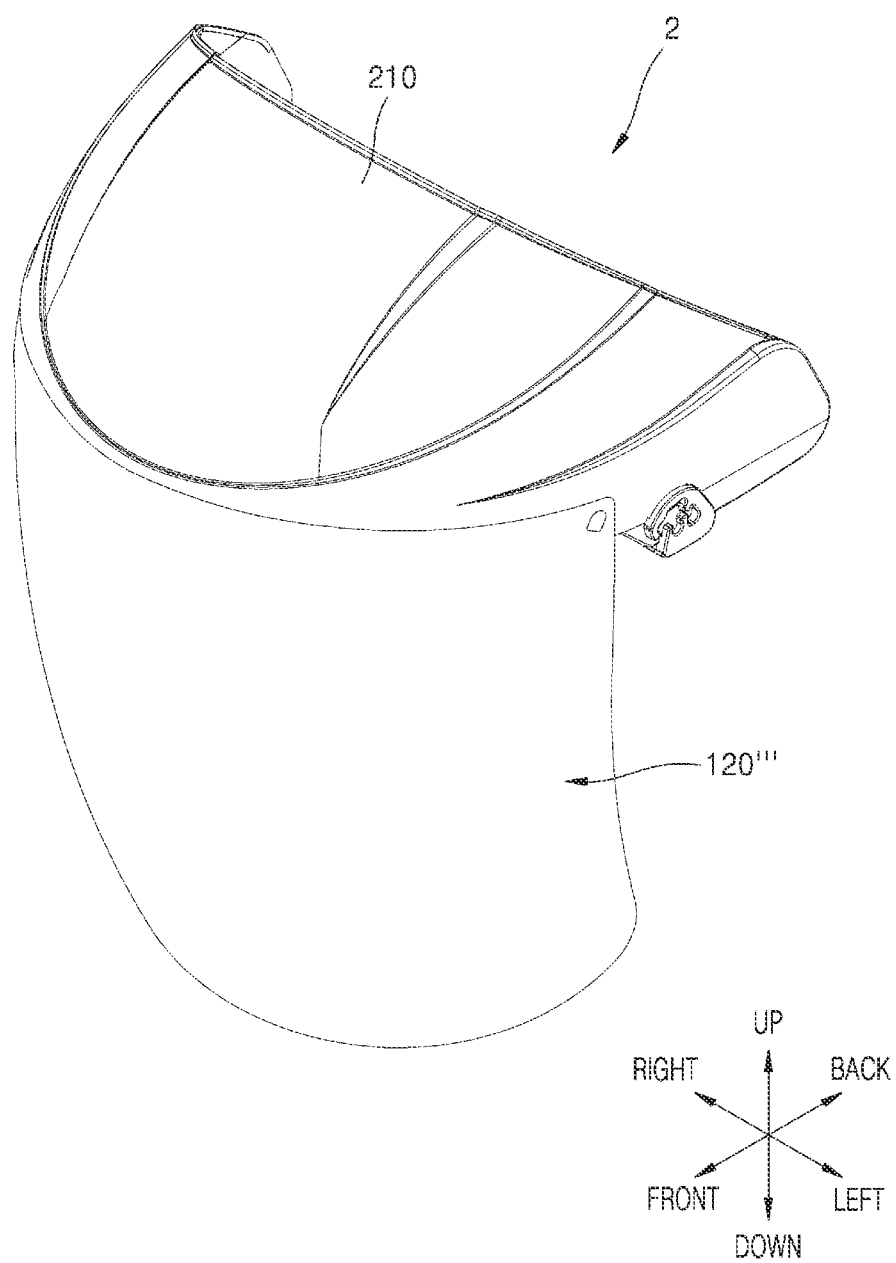
FIG. 11 is a schematic perspective view of an eye protection structure according to another embodiment of the present disclosure.

FIG. 11 is a schematic perspective view of an eye protection structure according to another embodiment of the present disclosure.

FIG. 11 illustrates an eye protection structure 2 according to another embodiment of the present disclosure, having a structure in which a main body 210 provided in the eye protection structure 2 extends to cover a part of the user's head, for example, a forehead, a crown and a part of an occipital region. In this case, a window 120''' may have an area that entirely covers the user's face. The window 120''' may have the feature described with reference to FIGS. 3 to 6 above, for example, the feature to reduce eye fatigue of the user who recognizes an external object through the window 120'''. In addition, it may also have the feature of having the rib described with reference to FIG. 7A.

In the window 120, 120', 120", or 120''' described with reference to FIGS. 1 to 11, the transmissive portion has the curved surface in a cross-section in the left and right direction as illustrated in FIG. 4, and the transmissive portion has a relatively flat cross-section in the vertical direction as illustrated in FIG. 2, but the present disclosure is not limited thereto. As another embodiment, as will be described later with reference to FIGS. 12A to 14B, a window may have a curved surface in a cross-section in a vertical direction as well as a cross-section in a left and right direction.

Figure 12A:
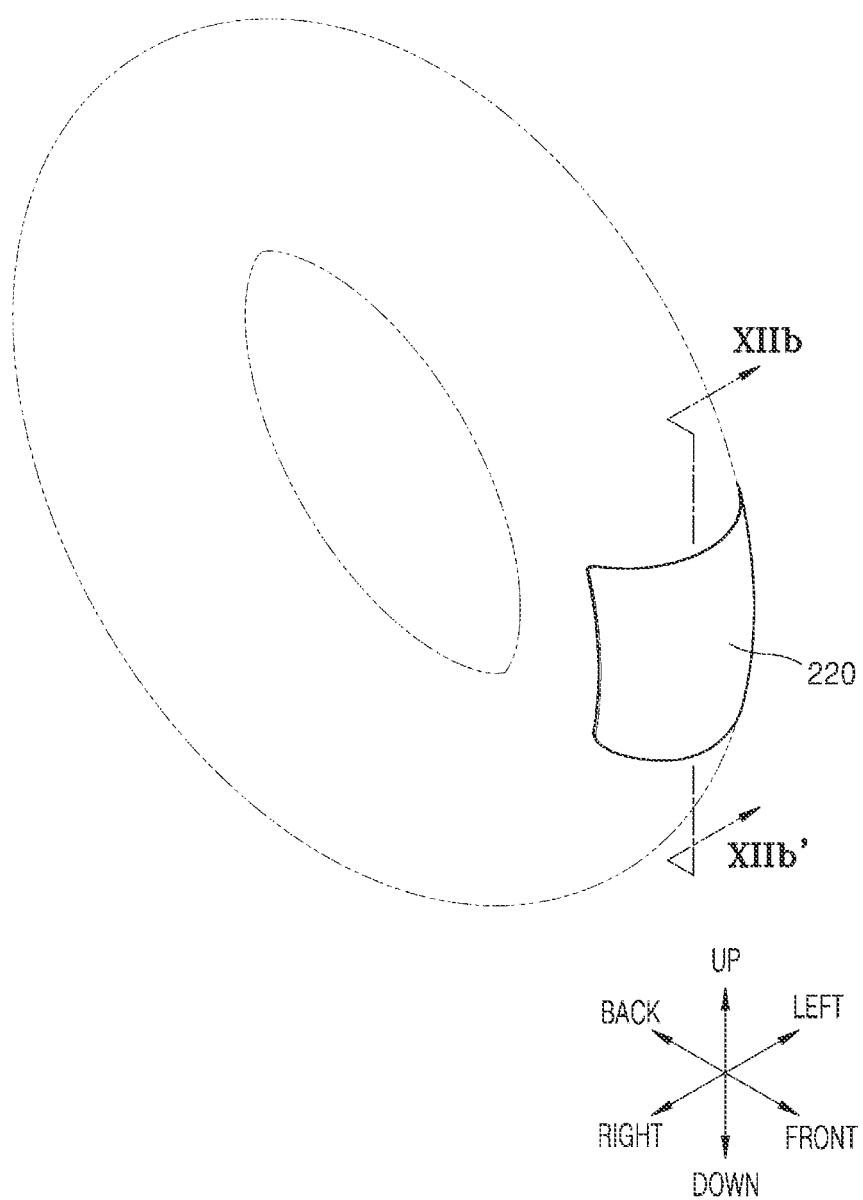
FIG. 12A is a schematic perspective view of a window according to another embodiment of the present disclosure.
Figure 12B:
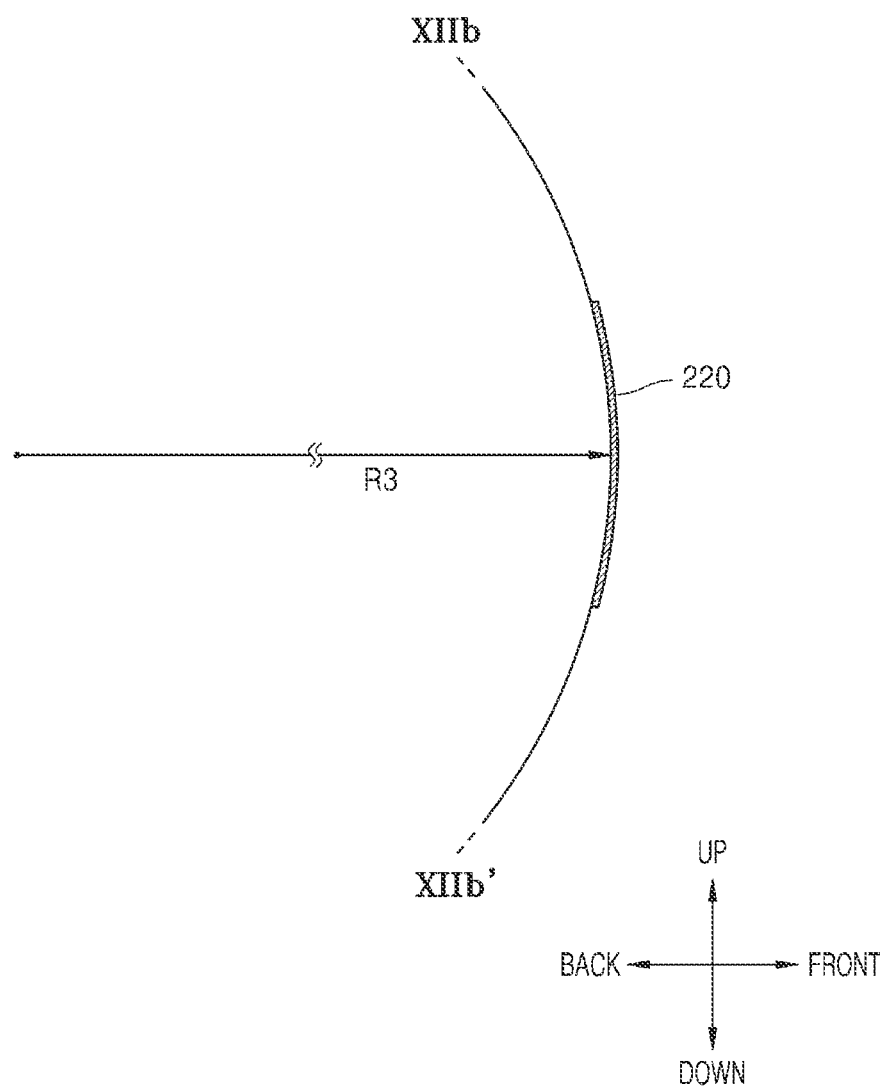
FIG. 12B is a cross-sectional view taken along line XIIb-XIIb' of the window of FIG. 12A.

FIG. 12A is a schematic perspective view of a window according to another embodiment of the present disclosure, and FIG. 12B is a cross-sectional view taken along line XIIb-XIIb' of the window of FIG. 12A. A window 220 illustrated in FIGS. 12A and 12B may have features as described above with reference to FIGS. 4 and 6 in a cross-section in the left and right direction.

Referring to FIGS. 12A and 12B, the window 220 includes a cross-section in a vertical direction that is a curved surface, and the curved surface may be placed on a toroid. On a cross-sectional view of the window 220 in the vertical direction, a third radius of curvature R3 of an inner surface of the window 220 may be greater than the first radius of curvature R1 and the second radius of curvature R2 described in FIGS. 4 and 6 above.

Figure 13A:
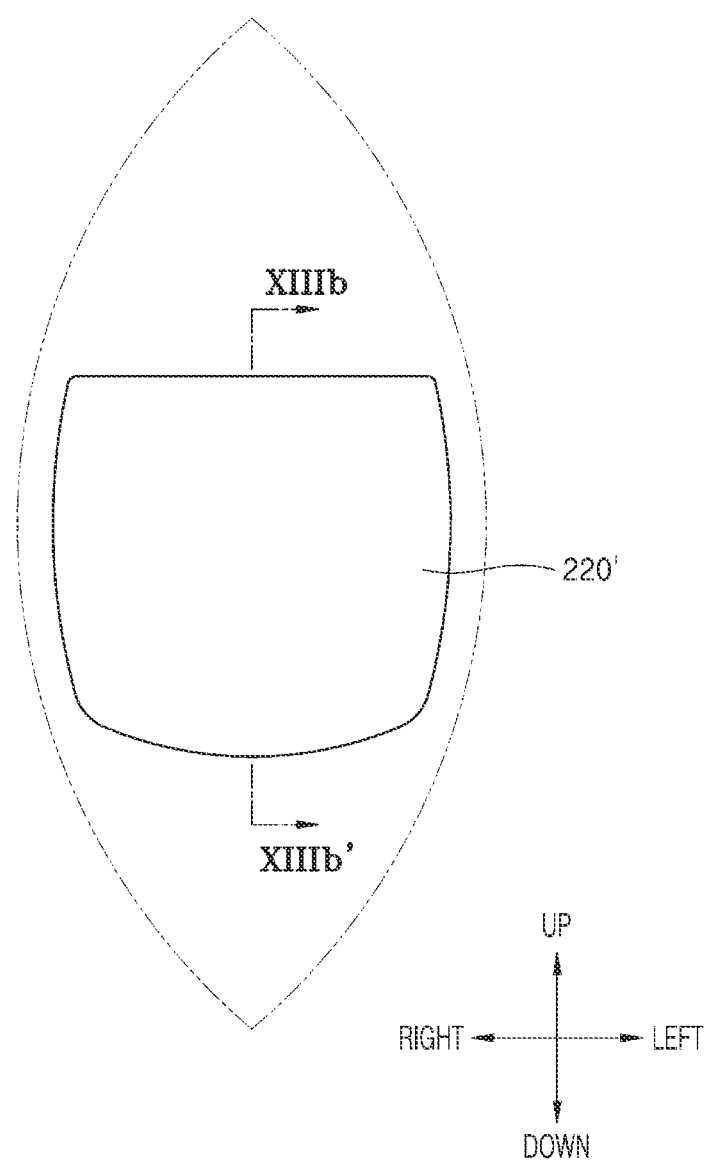
FIG. 13A is a schematic perspective view of a window according to another embodiment of the present disclosure.
Figure 13B:
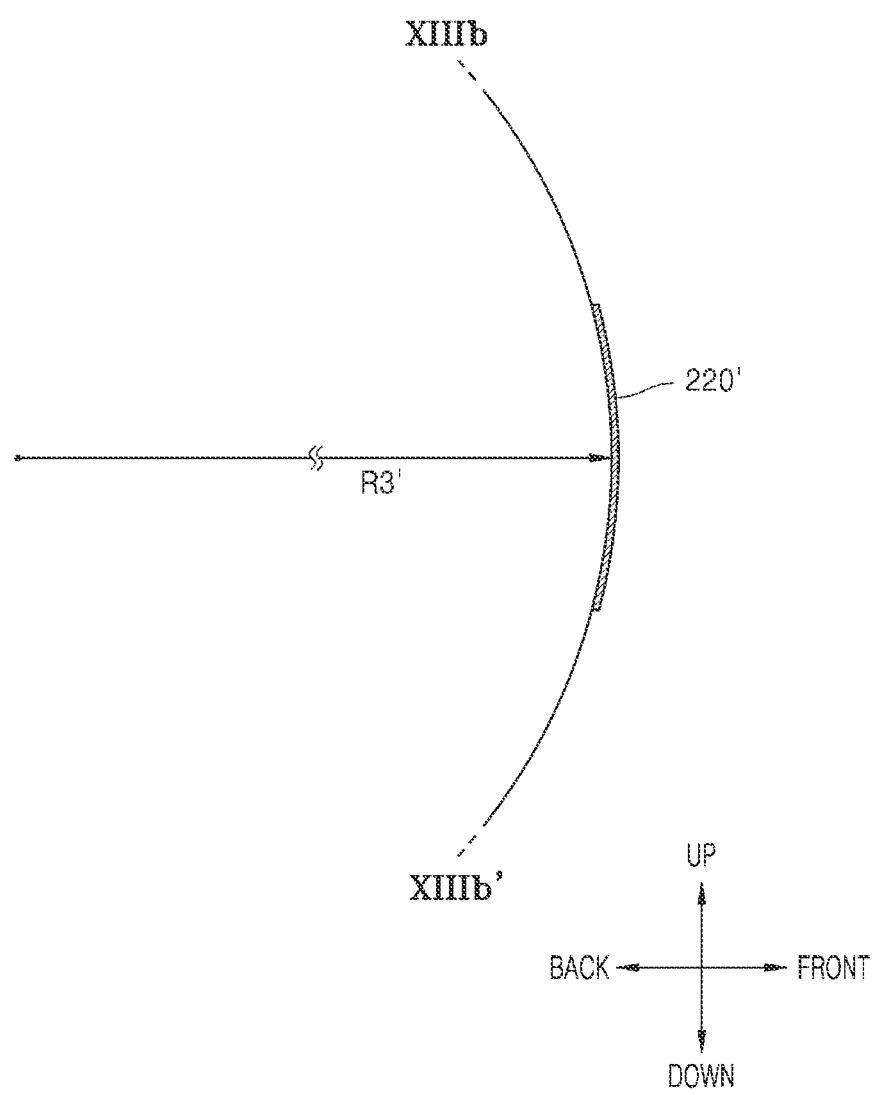
FIG. 13B is a cross-sectional view taken along line XIIIb-XIIIb' of the window of FIG. 13A.

FIG. 13A is a schematic perspective view of a window according to another embodiment of the present disclosure, and FIG. 13B is a cross-sectional view taken along line XIIb-XIIIb' of the window of FIG. 13A.

A window 220' illustrated in FIGS. 13A and 13B may have features in the cross-section in the left and right direction as described above with reference to FIGS. 4 and 6.

Referring to FIGS. 13A and 13B, the window 220' includes a cross-section in a vertical direction that is a curved surface, and may be placed on a toric. On a cross-sectional view of the window 220' in the vertical direction, a third radius of curvature R3 of an inner surface of the window 220' may be greater than the first radius of curvature R1 and the second radius of curvature R2 described in FIGS. 4 and 6 above. Alternatively, the third radius of curvature R3 of the inner surface of the window 220' may be smaller than the first radius of curvature R1 and the second radius of curvature R2 described in FIGS. 4 and 6 above.

Figure 14A:
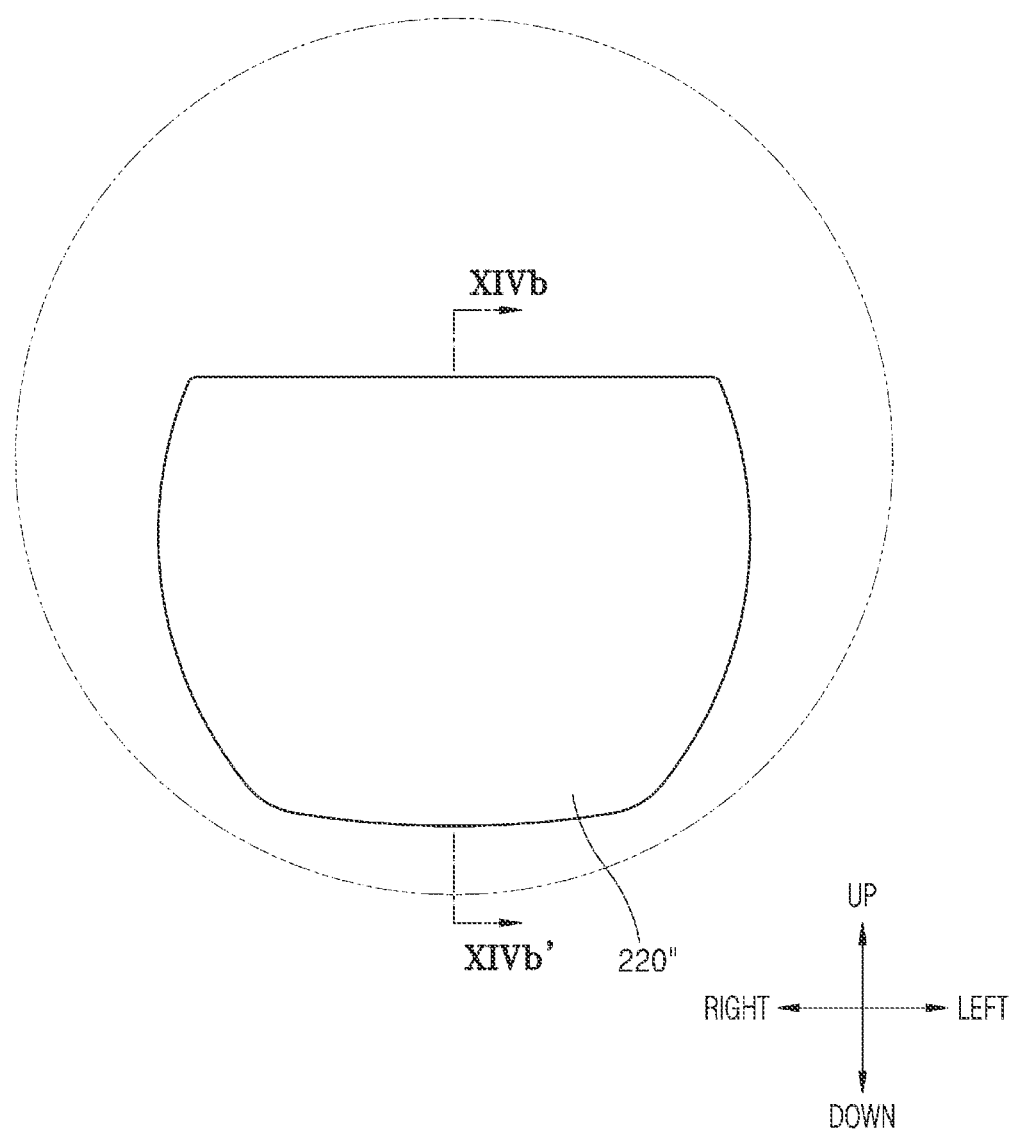
FIG. 14A is a schematic perspective view of a window according to another embodiment of the present disclosure.
Figure 14B:
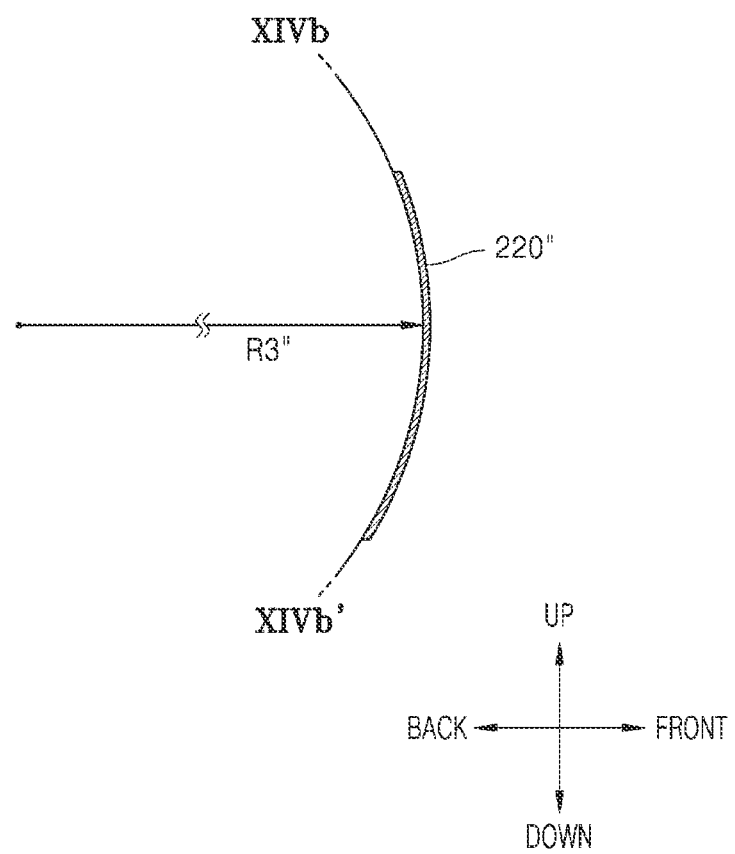
FIG. 14B is a cross-sectional view taken along line XIVb-XIVb' of the window of FIG. 14A.

FIG. 14A is a schematic perspective view of a window according to another embodiment of the present disclosure, and FIG. 14B is a cross-sectional view taken along line XIVb-XIVb' of the window of FIG. 14A.

A window 220" illustrated in FIGS. 14A and 14B may have features in the cross-section in the left and right direction as described above with reference to FIGS. 4 and 6.

As illustrated in FIGS. 14A and 14B, the window 220" includes a cross-section in a vertical direction that is a curved surface, and may be placed on a sphere. On the cross-sectional view in the vertical direction of the window 220", a third radius of curvature R3" of an inner surface of the window 220" may have substantially the same value as the first radius of curvature R1 or the second radius of curvature R2 described in FIGS. 4 and 6 above.

The window 120, 120', 120", 120''', or 220 described with reference to FIGS. 1 to 14 is coupled to the main body 110 or 210, the main body 110 or 210) covers a frontal portion of the user as illustrated in FIGS. 1 and 11. For example, the eye protection structure may include a welding helmet as illustrated in FIG. 1 or may include a face shield as illustrated in FIG. 11, but the present disclosure is not limited thereto. As another embodiment, the window having the above-described features may be coupled to a goggle-type or glasses-type main body, and an eye protection structure that does not cover the user's frontal portion may also correspond to an embodiment of the present disclosure. For example, the window coupled to the goggle-type or glasses-type main body may have the feature(s) as described with reference to FIGS. 3 to 10B and/or the feature(s) as described with reference to FIGS. 12A to 14B. Accordingly, effects such as eye protection functions such as preventing the user's vision deterioration or fatigue accumulation, and/or increasing a coupling force with the main body or preventing deformation of the window due to external factors (force or heat) may be achieved in the same manner.

As described above, the present invention has been described with reference to an embodiment shown in the drawings, but this is only exemplary, and those of ordinary skill in the art will understand that various modifications and variations of the embodiment are possible therefrom. Therefore, the true technical protection scope of the present invention should be determined by the technical spirit of the appended claims.

The invention claimed is:

1. An eye protection structure for protecting a worker, the eye protection structure comprising a window convex outward to cover both eyes of the worker, wherein the window includes a monolithic transmissive portion, wherein the transmissive portion includes an inner surface facing the worker's face and an outer surface opposite to the inner surface, a first radius of curvature of the outer surface of the transmissive portion and a second radius of curvature of the inner surface of the transmissive portion are different from each other, and a thickness of a central portion of the transmissive portion is greater than a thickness of an edge portion of the transmissive portion, wherein the window further includes an opaque portion having a smaller transmittance than the transmissive portion, wherein the opaque portion includes an uneven surface.

2. The eye protection structure of claim 1, wherein the second radius of curvature is smaller than the first radius of curvature.

3. The eye protection structure of claim 2, wherein the second radius of curvature depends on at least one of the first radius of curvature, the thickness of the central portion, and a refractive index of the transmissive portion.

4. The eye protection structure of claim 2, wherein the transmissive portion satisfies the following condition:

$(R1-t1+t1/n)-1 < R2 < R1$ wherein

R1 represents the first radius of curvature, t1 represents the thickness of the central portion of the transmissive portion, n represents the refractive index of the transmissive portion, and R2 represents the second radius of curvature.

5. The eye protection structure of claim 1, wherein the window includes a resin material.

6. The eye protection structure of claim 1, wherein a center of the first radius of curvature and a center of the second radius of curvature are apart from each other.

7. The eye protection structure of claim 1, wherein the window further includes a rib disposed inside the transmissive portion.

8. The eye protection structure of claim 7, wherein the rib extends along a direction crossing the inner surface of the transmissive portion.

9. The eye protection structure of claim 1, wherein the uneven surface is positioned on an inner surface or an outer surface of the opaque portion.

10. The eye protection structure of claim 1, wherein the opaque portion entirely surrounds the transmissive portion.

11. The eye protection structure of claim 1, wherein the transmissive portion is free of a light-darkening filter between the outer and inner surfaces.

* * * * *